US008086323B2

(12) United States Patent
Reghabi et al.

(10) Patent No.: US 8,086,323 B2
(45) Date of Patent: Dec. 27, 2011

(54) IMPLANTABLE MULTI-PARAMETER SENSING SYSTEM AND METHOD

(75) Inventors: Bahar Reghabi, Marina del Rey, CA (US); Rebecca Gottlieb, Culver City, CA (US); Rajiv Shah, Rancho Palos Verdes, CA (US); Bradley Enegren, Moorpark, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 1022 days.

(21) Appl. No.: 10/669,426

(22) Filed: Sep. 23, 2003

(65) Prior Publication Data

US 2005/0065556 A1    Mar. 24, 2005

(51) Int. Cl.
*A61N 1/05* (2006.01)
(52) U.S. Cl. ..................................... 607/116
(58) Field of Classification Search .......... 607/6, 21–23, 607/17–18, 116, 119; 600/300–302, 323
See application file for complete search history.

(56) References Cited

U.S. PATENT DOCUMENTS

| | | | | |
|---|---|---|---|---|
| 4,608,986 A | * | 9/1986 | Beranek et al. | 607/123 |
| 4,703,756 A | | 11/1987 | Gough et al. | |
| 4,844,871 A | * | 7/1989 | Polaschegg | 422/81 |
| 5,999,848 A | | 12/1999 | Gord et al. | 607/2 |
| 6,081,736 A | | 6/2000 | Colvin et al. | |
| 6,164,284 A | * | 12/2000 | Schulman et al. | 128/899 |
| 6,248,067 B1 | | 6/2001 | Causey, III et al. | |
| 6,304,786 B1 | * | 10/2001 | Heil et al. | 607/126 |
| 6,312,393 B1 | | 11/2001 | Abreu | |
| 6,501,983 B1 | * | 12/2002 | Natarajan et al. | 600/517 |
| 7,025,778 B2 | * | 4/2006 | Hayashi et al. | 623/1.34 |
| 2002/0023852 A1 | * | 2/2002 | Mcivor et al. | 206/305 |
| 2002/0193836 A1 | * | 12/2002 | Schmidt | 607/9 |
| 2003/0050547 A1 | | 3/2003 | Lebel et al. | |

FOREIGN PATENT DOCUMENTS

| | | | |
|---|---|---|---|
| WO | WO 00/13003 | | 3/2000 |
| WO | WO 00/25863 | | 5/2000 |
| WO | WO 01/22874 | * | 4/2001 |
| WO | WO 02/102267 A1 | | 12/2002 |

OTHER PUBLICATIONS

Mathias ,JR, Sninsky CA, Millar HD, Clench MH, Davis RH. Development of an Improved Multi-Pressure-Sensor Probe for Recording Muscle Contraction in Human Intestine. Digestive Diseases and Sciences, vol. 30, No. 2 (Feb. 1985), pp. 119-123. Germany.

(Continued)

*Primary Examiner* — Scott Getzow
*Assistant Examiner* — Amanda Patton

(57) ABSTRACT

A system and method of sensing multiple parameters. The method may include implanting an implantable sensor in a patient and reading an output from at least one of the implantable sensing elements. The implantable sensor may have a housing within which are disposed a plurality of implantable sensing elements. At least one of the implantable sensing elements may respond to lactate. In addition, a medical professional may administer to the patient for myocardial ischemia, myocardial infarction angina, sepsis based on the output read. A medical professional may also administer to the patient having an implantable cardiovascular defibrillator or who is receiving extracorporeal membrane oxygenation. The method may be used in a surgical or intensive care environment.

71 Claims, 11 Drawing Sheets

OTHER PUBLICATIONS

Latham RD, Westerhof N, Sipkema P, Rubal BJ, Reuderink P, Murgo JP. Regional wave travel and reflections along the human aorta: a study with six simultaneous micromanometric pressures. Circulation 72, No. 6, 1257-1 269, 1985. USA.

Brooke Army Medical Center (BAMC) Catheterization Records 1985-1992 (includes records from 1975 and 1973), San Antonio, Texas.

Millar Instruments Mikro-Tip® Catheter Pressure Transducers and Accessories Product Information, Feb. 1, 1985, Houston, Texas.

Millar Mikro-tip(R) Catheter Pressure Transducers Product Information and Price List, Jan. 1, 1984, Houston, Texas.

Office Action for European Application No. 04782904.9 dated Jul. 1, 2008.

Office Action for European Application No. 04782904.9 dated Sep. 5, 2006.

Search Report for PCT International Application No. PCT/US2004/028505 dated Dec. 14, 2004.

Foreign action dated May 18, 2010 from related Japanese application No. 2006-528015.

* cited by examiner

```
50  ┌─────────────────┐
    │ Position sensor │
    └────────┬────────┘
             │
             ▼
    ┌─────────────────┐
    │ Monitor lactate,│
    │  blood oxygen   │
52  │ saturation, pH in│
    │ connection with │
    │   myocardial    │
    │    ischemia    │
    └────────┬────────┘
             │
             ▼
    ┌─────────────────┐
    │   Asses risk/   │
54  │administer therapy│
    │ for myocardial  │
    │    ischemia     │
    └─────────────────┘
```

Fig. 4

IMPLANTABLE MULTI-PARAMETER SENSING SYSTEM AND METHOD

BACKGROUND

1. Field of the Invention

Embodiments of the present invention relate to biomedical sensor technology and, in particular, to implantable, multi-parameter sensing systems and methods.

2. Description of Related Art

Continuous parameter measurement is important in the detection and monitoring of disease in patients. The ability to monitor biological or physiological parameters, analytes and other parameters in a patient in emergency rooms, intensive care units and other hospital settings is critical in stabilizing patients and reducing mortality rates. The monitoring of blood oxygen saturation, blood pressure, glucose, lactate, temperature, ion concentration, such as potassium, for example, and pH, for example, provides an indication of the state of tissue oxygen balance in the patient, knowledge of which is crucial in preventing a patient from progressing toward a serious, debilitating medical condition or even death.

Various situations require prompt monitoring and response to a change in body chemistry or other patient parameters. For example, sepsis, a toxic condition resulting from the spread of bacteria or their products from a focus of infection, can lead to global tissue hypoxia, multiple organ failures, cardiovascular collapse and eventual death. Increased blood lactate concentrations and decreased mixed venous oxygen saturation are classic indicators of the early phases of septic shock. By monitoring these parameters, blood chemistry levels can be regulated and the incidence of sepsis decreased.

The prevention of sepsis is becoming increasingly important. Cases of sepsis occur more frequently in elderly persons than in younger populations. As the number of elderly persons nationwide and worldwide continues to increase, the number of cases of sepsis can be expected to increase as well.

Blood glucose is another parameter that requires monitoring in a medical setting in order to reduce injury and mortality rates. For example, for patients who are in an intensive care environment, especially those with diabetes, glucose monitoring is critical. If the amount of glucose in the diabetic patient's system is not maintained at proper levels, the patient may sustain serious or life-threatening injury. If too much glucose accumulates in the diabetic patient's system, the patient could become hyperglycemic, resulting in shortness of breath, nausea and vomiting at best or diabetic coma and death in the worst case. If there is too little glucose in the diabetic patient's system, the patient could become hypoglycemic, resulting in dizziness, sweating and headache at best and unconsciousness and death in the worst case.

Electrolyte and ion monitoring may have great potential for some electrolyte disorders. For example, low sodium or hyponatremia (an acute or chronic condition caused by kidney failure, pneumonia, meningitis, trauma, adrenal/pituitary gland insufficiency, congestive heart failure and cirrhosis) can cause water from the body fluids to move into the higher osmolarity tissue, causing the tissue to expand (edema). One clinical manifestation of this syndrome is increased brain pressure from cerebral edema. Potassium deficit (<3.5 mmol/L) has been linked with increased incidence of stroke in elderly individuals, especially those with arterial fibrillation. Additionally, serum potassium level has been a predictor of serious peri- and intra-operative arrhythmia, and postoperative arterial fibrillation.

Traditionally, the monitoring of patient parameters in a hospital or other medical setting has been accomplished by drawing a blood sample and sending the sample to a laboratory for analysis. This type of monitoring process, while well-established and providing accurate results, is time-consuming and, indeed, time-prohibitive in an emergency situation. By the time lab results return to an attending physician, the patient may have already entered into a serious state or even may have already died.

Some industry attempts have been made to provide continuous, immediate monitoring of patient parameters. For example, Diametrics Medical, Inc., has developed several sensing systems for monitoring patient parameters, such as the NEUROTREND Sensor and the PARATREND7+ Sensors. The NEUROTREND Sensor is a disposable, single-use device for the continuous measurement of intra cranial pH, $pCO_2$, $pO_2$, and temperature that is used in conjunction with an appropriate intracranial access device. The device incorporates optical sensors and thermocouples for the measurement of pH, $pCO_2$, and $pO_2$, and a thermocouple for temperature measurement. The NEUROTREND sensor indicates the perfusion and metabolic acidosis/alkalosis status of cerebral tissue in the vicinity of the sensor. The PARATREND7+ Sensors are disposable, single-use fiber optic devices for continuous measurement of pH, $pCO_2$, $pO_2$ and temperature, providing real-time oxygenation, ventilation and metabolic information for critically ill patients.

However, the NEUROTREND Sensors and the PARATREND7+ Sensors have limited capabilities. Optical sensors lose effectiveness quickly when proteins deposit on their surface, which is inevitable in the body. The NEUROTREND Sensors and the PARATREND7+ Sensors, which are based on optical sensors, thus, tend to lose their effectiveness quickly. Accordingly, medical professionals must still use conventional techniques for obtaining reliable, quantifiable parameter values in addition to the values indicated by the NEUROTREND Sensors and the PARATREND7+ Sensors when administering to patients.

To date, there have been no implantable sensors providing continuous, quantifiable, simultaneous measurement values for patient parameters. In particular, there have been no implantable sensors providing continuous, quantifiable, simultaneous measurement values for lactate, glucose, pH, temperature, venous oxygen pressure, venous oxygen concentration and potassium. An implantable, multi-parameter sensor that monitors one or more of glucose, lactate, pH, temperature, venous oxygen pressure, venous oxygen concentration and blood potassium could be used advantageously in hospital or medical settings, in critical care, emergency care and intensive care situations, in triage, surgery and in field applications. For example, because a patient's blood glucose concentration may increase during kidney dialysis, the monitoring of glucose, oxygen and temperature during dialysis may be helpful.

SUMMARY

It is therefore an object of embodiments of the present invention to provide a system and method for sensing and quantifying multiple parameters in a patient. It is a further object of embodiments of the present invention to provide a system and method for using an implantable, multi-parameter sensor that responds to a plurality of analytes simultaneously. It is yet a further object of embodiments of the present invention to provide a system and method for sensing multiple parameters that can be used in critical care, intensive care or emergency environments. It is yet a further object of embodiments of the present invention to provide a system and method for sensing multiple parameters that can provide continuous measurement of blood oxygen saturation, lactate, oxygen pressure, ion measurement, such as, potassium, hydrogen (pH) and sodium, for example, carbon dioxide, glucose and other ion concentrations.

A method of sensing multiple parameters may include implanting an implantable sensor at a single site in a patient, the implantable sensor having a housing within which are disposed a plurality of implantable sensing elements; and reading an output from at least one of the implantable sensing elements. A plurality of parameters may be read from the implantable sensor at the single site. The output read from at least one of the implantable sensing elements may be a quantifiable value. Also, at least one of the implantable sensing elements may be a biological parameter sensor, a physiological parameter sensor or an analyte sensor. Reading an output from at least one of the implantable sensing elements may include reading an output from the at least one implantable sensing element that responds to lactate, blood oxygen saturation, blood pressure, glucose, blood temperature, potassium or pH.

The method may also include administering therapy to the patient based on the output read from the at least one implantable sensing element. Administering therapy may include administering therapy for myocardial ischemia, myocardial infarction, sepsis, septic shock or angina. Administering therapy may also include adjusting a function or a placement of an implantable cardiovascular defibrillator disposed within the patient or administering therapy for a patient receiving extracorporeal membrane oxygenation. The method may also include classifying a severity of a condition of the patient or classifying a worsening condition of the patient. The method may be used in a surgical environment in an intensive care environment.

A method of evaluating a patient may include implanting an implantable sensor at a single site in a patient, the implantable sensor having a housing within which are disposed a plurality of implantable sensing elements; reading an output from at least one of the implantable sensing elements; and evaluating the patient based on the output read from the at least one implantable sensing element. A plurality of parameters may be read from the implantable sensor at the single site. The output read from at least one of the implantable sensing elements may be a quantifiable value. Evaluating the patient may include evaluating the patient based on an output from the at least one implantable sensing element that responds to lactate or from at least one implantable sensing element that responds to blood oxygen saturation, blood pressure, glucose, blood temperature, potassium or pH.

Evaluating the patient may also include evaluating the patient for myocardial ischemia, myocardial infarction, angina, sepsis or septic shock or any other condition or situation. Evaluating the patient may also include evaluating the patient having an implantable cardiovascular defibrillator or evaluating the patient receiving extracorporeal membrane oxygenation.

BRIEF DESCRIPTION OF THE DRAWINGS

FIG. 4 shows a method for using an implantable, multi-parameter sensor according to an embodiment of the present invention.

DETAILED DESCRIPTION

In the following description of preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the preferred embodiments of the present invention.

Although the following description is directed primarily toward systems and methods for sensing multiple parameters in a patient, embodiments of the present invention may be used in a variety of capacities and applications. For example, embodiments of the present invention may be used for critical care, intensive care or emergency environments or in triage, surgery and in field applications or, for example, in particular medical or surgical procedures, such as dialysis or cardiac bypass, for example. Also, embodiments of the present invention may be used in hospitals to simultaneously measure multiple analytes. Generally, embodiments of the present invention may be adapted for use in any type of medical or hospital situation where simultaneous measurement of biological or physiological parameters or analytes is desired.

Figure 1:
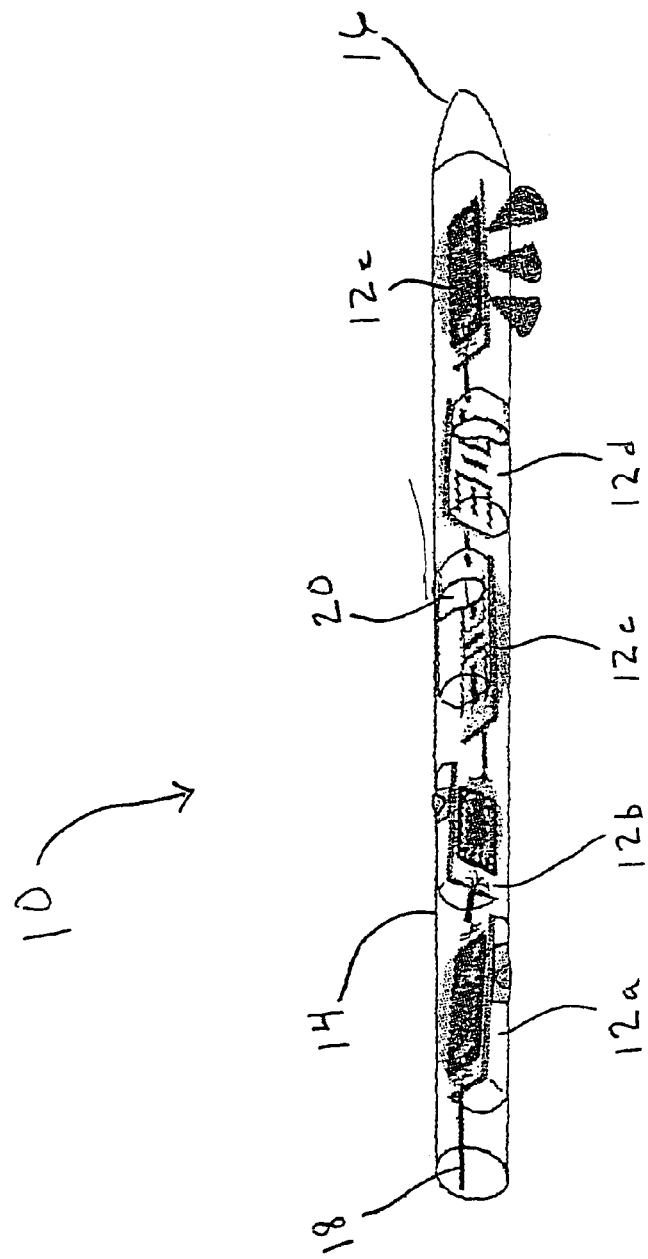
FIG. 1 shows a perspective view of an apparatus for sensing multiple parameters according to an embodiment of the present invention.

An apparatus for sensing multiple parameters 10 according to an embodiment of the present invention may be seen in FIG. 1. The apparatus for sensing multiple parameters 10 shown in FIG. 1 includes, but is not limited to, a housing 14, a plurality of sensors 12a-12e, a tip 16 and an interconnect 18. The housing 14 may also include one or more apertures 20 for permitting physical or other contact between fluids in the body and sensing elements located on each of the plurality of sensors 12a-12e.

Each of the plurality of sensors 12a-12e may be designed to sense one or more parameters. For example, each of the plurality of sensors 12a-12e may be designed to sense a biological or physiological parameter in a patient, such as, for example, blood oxygen saturation, blood pressure, blood temperature, or blood pH. Also, each of the plurality of sensors 12a-12e may be designed to sense a parameter such as an analyte in a patient, such as, for example, glucose, lactate, potassium, pH, sodium, $pCO_2$, $pO_2$, $SvO_2$, $pvO_2$, temperature and urea. Accordingly, given the various mechanisms required to sense various parameters, each of the plurality of sensors 12a-12e may be designed as an electrochemical sensor, a potentiometric sensor, a current sensor, a physical quantity sensor, an optical sensor or other type of sensor, dictated by the parameter being measured. In addition, the output of one or more of the plurality of sensors 12a-12e may be a quantifiable value. In other words, a measurement may be made by one or more of the plurality of sensors 12a-12e such that a quantifiable or absolute value is returned by the sensor.

Although the embodiment of the present invention shown in FIG. 1 includes five sensors, embodiments of the present invention may be designed with any number of sensors desired or necessary for a particular application. For example, an embodiment of the present invention shown in reference to the flowchart in FIG. 5 includes, without limitation, three sensors which monitor the lactate level, the blood oxygen saturation level, and the pH level in connection with the particular application of administering therapy for myocardial infarction or angina.

The plurality of sensors 12a-12e shown in FIG. 1 are "daisy-chained" together via the interconnect 18. Because "daisy-chaining" modules is facilitated by digital addressing, each of the plurality of sensors 12a-12e shown in the embodiment of FIG. 1 includes an analog-to-digital (A/D) converter integrated circuit as well as a power supply for powering the integrated circuit, such as, for example, a capacitor. Thus, because each of the plurality of sensors 12a-12e includes an onboard A/D, the information leaving the housing 14 on the interconnect 18 is in digital form.

Also, each of the plurality of sensors 12a-12e may be individually addressed by a remote device, such as, for example, a computer or other controller. The addressing schemes may be any scheme common in the industry and may include, without limitation, frequency modulation or time modulation schemes.

The housing 14 may be fabricated in a variety of ways. For example, the housing 14 may be a single, standard catheter that is flexible for vascular placement. If the housing 14 is a flexible catheter, the apparatus for sensing multiple parameters 10 may be placed independently in the body. In addition, the housing 14 may be one lumen of a multi-lumen catheter or may be part of a central venous line or sheath. According to an embodiment of the present invention, the housing 14 may be made of silicone or a polyethylene, for example.

According to an embodiment of the present invention, the tip 16 may be an ogive shape, i.e., a "bullet nose." An ogive-shaped tip 16 may optimize a flow field around the apparatus for sensing multiple parameters 10 and, being curved, may be less likely to gouge the patient during insertion. According to another embodiment of the present invention, the tip 16 may have some sort of structure, such as, for example, a screw anchor or other structure, allowing it to be fixed into tissue.

Figure 2:
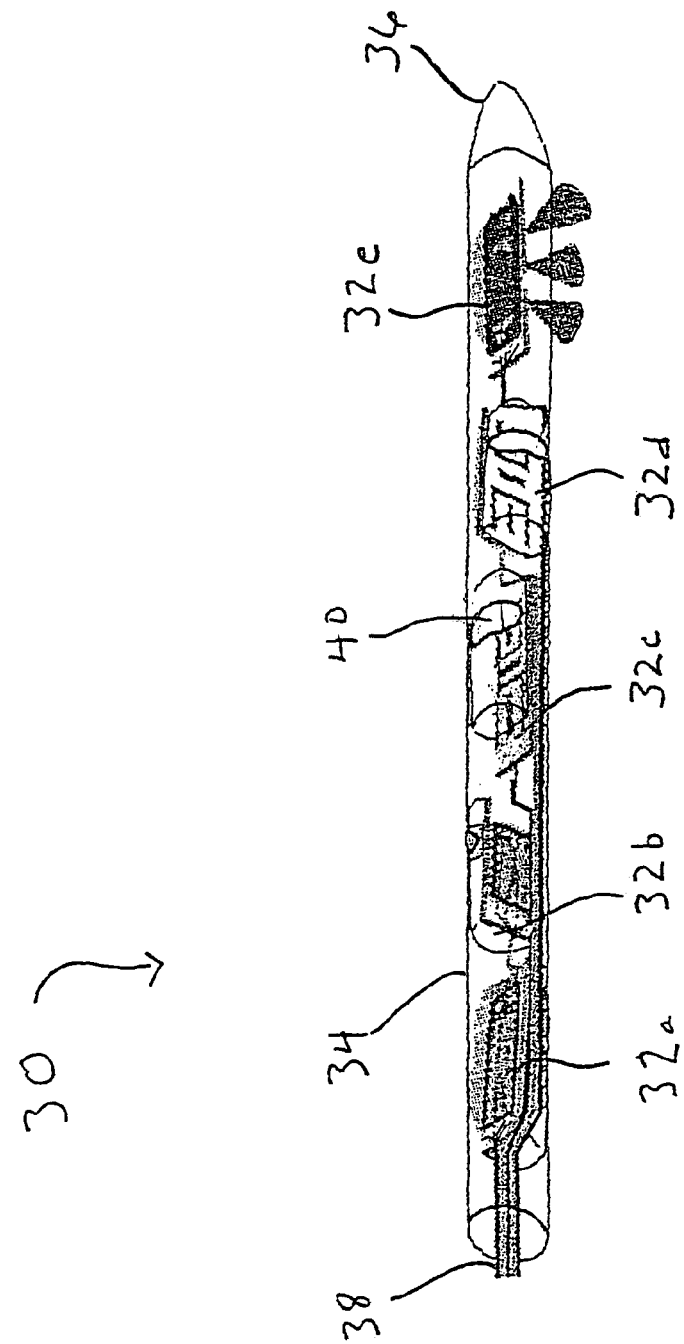
FIG. 2 shows a perspective view of another apparatus for sensing multiple parameters according to an embodiment of the present invention.

FIG. 2 shows an apparatus for sensing multiple parameters 30 according to another embodiment of the present invention. The apparatus for sensing multiple parameters 30 includes, but is not limited to, a plurality of sensors 32a-32e, a housing 34, a tip 36 and an interconnect 38. The housing 34 may also include one or more apertures 40 allowing fluids in the body to come into physical contact with the sensors 32a-32e.

Whereas each of the plurality of sensors 12a-12e of FIG. 1 were daisy-chained together, the plurality of sensors 32a-32e in FIG. 2 operate independently of one another and are individually wired. In other words, according to the embodiment of the present invention shown in FIG. 2, each of the plurality of sensors 32a-32e has a wire connected to it that is routed out of the housing 34 such that the interconnect 38 is actually a plurality of interconnects. Because there is no daisy-chain configuration in the embodiment of the invention shown in FIG. 2, there is no need for each of the plurality of sensors 32a-32e to be digitally addressable. Each of the plurality of sensors 32a-32e may transmit or receive an analog signal; there is no requirement to include an onboard A/D integrated circuit and associated power supply. Without the A/D integrated circuit and associated power supply, the "wired" sensing apparatus 30 according to the embodiment of the present invention shown in FIG. 2 may have a reduced size, making it flexible and desirable for medical and/or surgical use.

Embodiments of the present invention need not be limited to a "daisy-chained" sensing apparatus as shown in FIG. 1 or a "wired" sensing apparatus as shown in FIG. 2. Embodiments of the present invention may also include, without limitation, a combination of daisy-chained and wired configurations.

The sensors 12a-12e and 32a-32e shown in the embodiments of the invention of FIG. 1 and FIG. 2 may be physically disposed in a variety of ways. For example, the plurality of sensors 12a-12e shown in FIG. 1 and the plurality of sensors 32a-32e shown in FIG. 2 are arranged in a "perpendicular" fashion. In other words, in the embodiments of the invention shown in FIGS. 1 and 2, each sensor is aligned perpendicularly or is "on its side" relative to the sensor adjacent to it. Thus, according to embodiments of the present invention, flexibility in position and/or orientation may be achieved. For example, according to embodiments of the present invention, a drug may be dosed in a perpendicular fashion on one half of the catheter while a parameter may be measured on another half of the catheter. Also, in embodiments of the invention in which all sensing elements are disposed on one side or the catheter, for example, the catheter may be rotated or positioned in multiple orientations to determine a variance in readings for a particular environment, thus indicating whether an environment is "well-mixed."

Figure 3:
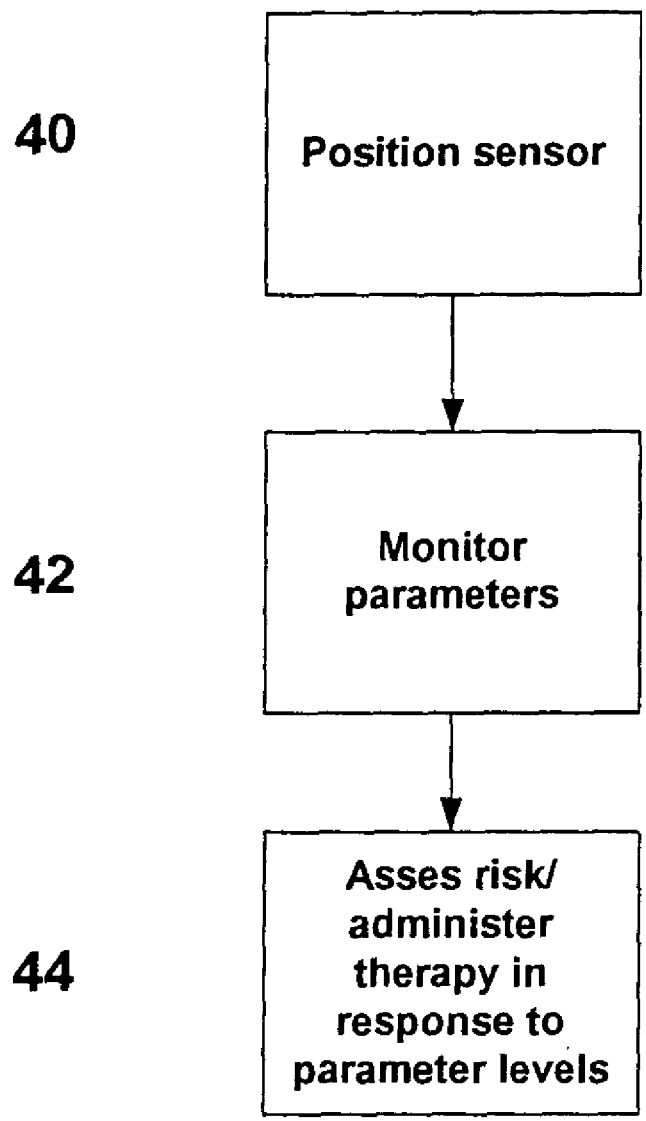
FIG. 3 shows a generalized method for using an implantable, multi-parameter sensor according to an embodiment of the present invention.

A generalized method for using an implantable, multi-parameter sensor according to an embodiment of the present invention is shown in FIG. 3. According to the embodiment of the invention shown in FIG. 3, an implantable, multi-parameter sensor is positioned in a patient at step 40. The implantable, multi-parameter sensor may be inserted into the vasculature. According to other embodiments of the present invention, the implantable, multi-parameter sensor may be positioned in the peritoneal or may be positioned subcutaneously, or, for example, may be positioned in ventricular spaces, neurological spaces, such as the spine or brain, for example, intramuscular, myocardial, or pericardial spaces, and all vascular (venous and arterial) spaces. According to embodiments of the present invention, the implantable, multi-parameter sensor may also be position outside the body, for example, in an extracorporeal membrane oxygenation (ECMO) system.

At step 42, parameters are monitored using the implantable, multi-parameter sensor. According to embodiments of the present invention, a variety of parameters may be monitored. For example, lactate, blood oxygen saturation, potassium pH, blood pressure, glucose and blood temperature may be monitored. In addition, the parameters monitored may be monitored continuously or may be used to trigger alarms. According to other embodiments of the present invention, the parameters monitored may be used to suggest treatment for a patient based on measured values. Also, embodiments of the invention may be used in a variety of applications. For example, because a patient's blood glucose concentration may increase during kidney dialysis, embodiments of the invention may be used to monitor glucose, oxygen and temperature during dialysis. Also, for example, embodiments of the invention may be used to monitor parameters during surgical procedures, such as cardiac bypass, for example, or during triage.

At step 44, a risk level may be assessed or a therapy may be administered in response to the parameter levels sensed using the implantable, multi-parameter sensor. For example, based on the sensed level of a particular parameter, a medical professional may determine that the patient is at high-risk for a debilitating medical condition and an appropriate course of action may be commenced. According to another embodiment of the present invention, based on the sensed level of a particular parameter, a particular type of therapy may be administered, such as, for example, delivery to the patient of a particular drug.

A method for using an implantable, multi-parameter sensor in connection with myocardial ischemia according to an embodiment of the present invention is shown in FIG. 4. Myocardial ischemia, a condition in which oxygen deprivation to the heart muscle is accompanied by inadequate removal of metabolites because of reduced blood flow or perfusion, occurs due to an imbalance between myocardial oxygen supply and demand. According to embodiments of the present invention, myocardial ischemia may be monitored using an implantable, multi-parameter sensor.

According to an embodiment of the present invention shown in FIG. 4, an implantable, multi-parameter sensor is positioned in a patient at step 50. The implantable, multi-parameter sensor may be inserted into the vasculature. According to other embodiments of the present invention, the implantable, multi-parameter sensor may be positioned in the peritoneal or may be positioned subcutaneously or, for example, may be positioned in ventricular spaces, neurological spaces, such as the spine or brain, for example, intramuscular, myocardial, or pericardial spaces, and all vascular (venous and arterial) spaces. According to embodiments of the present invention, the implantable, multi-parameter sensor may also be position outside the body, for example, in an ECMO system.

At step 52, a variety of parameters may be monitored in connection with myocardial ischemia using the implantable, multi-parameter sensor. According to embodiments of the present invention, lactate levels blood oxygen saturation, base deficit and pH, for example, may be monitored in connection with myocardial ischemia. Also, these and other parameters may be continuously monitored. Insufficient myocardial ischemia (or perfusion) may lead to irreversible cell damage and/or myocardial infarction. Also, the transition from myocardial ischemia to myocardial infarction happens over the course of several hours and, during this period, blood lactate concentrations elevate and remain elevated until tissue reperfusion.

At step 54, a risk may be assessed or a therapy administered for myocardial ischemia. Because blood lactate concentrations elevate and remain elevated during the transition from myocardial ischemia to myocardial infarction, the monitoring of lactate concentrations may be a predictor of heart attacks. Thus, if high levels of lactate are monitored using the implantable, multi-parameter sensor, the risk of heart attack may be assessed and appropriate medication administered. Also, in the case of a myocardial infarction, "clot-busting" drugs need to be administered within the first few hours of the event.

Figure 5:
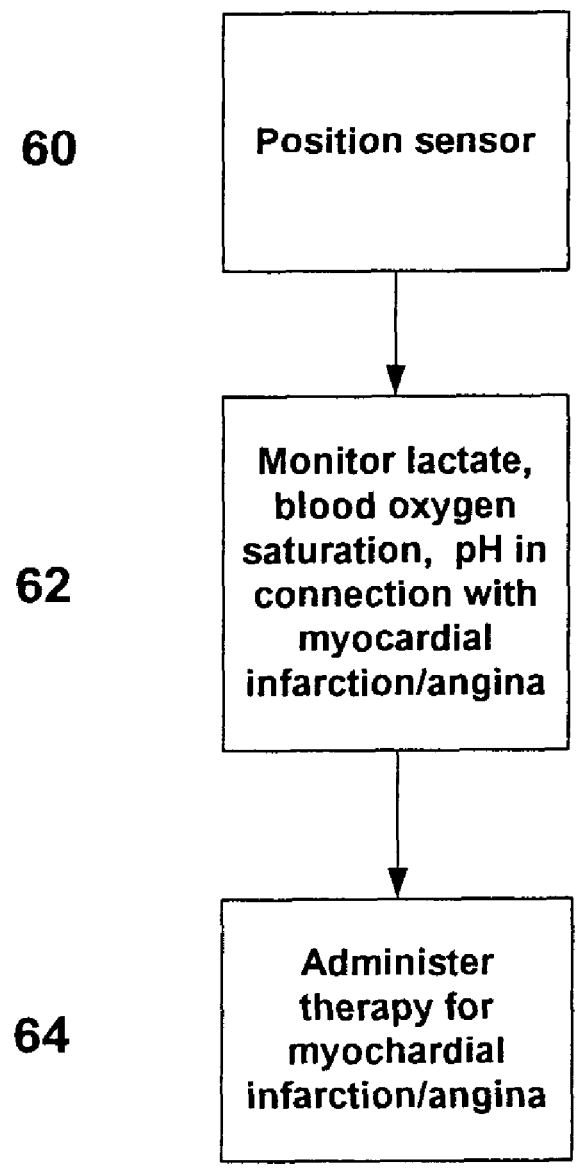
FIG. 5 shows another method for using an implantable, multi-parameter sensor according to an embodiment of the present invention.

A method for using an implantable, multi-parameter sensor in connection with myocardial infarction or angina according to an embodiment of the present invention is shown in FIG. 5. Myocardial infarction implies a death of heart muscle cells resulting from lack of oxygen supply and supply of other nutrients due to closure of the coronary artery. Lack of oxygen, otherwise known as tissue hypoxia, or oxygen imbalance, causes tissue metabolism to shift from aerobic to anaerobic. This shift results in increased tissue and blood lactate concentrations. Global tissue hypoxia may indicate serious illness and may precede multiple organ failure and death.

Angina is a discomfort experienced in the chest, arms neck or back by patients with coronary artery disease and indicates that the heart muscle is not getting enough blood. According to embodiments of the present invention, myocardial infarction and angina may be monitored using an implantable, multi-parameter sensor.

According to an embodiment of the present invention shown in FIG. 5, an implantable, multi-parameter sensor is positioned in a patient at step 60. The implantable, multi-parameter sensor may be inserted into the vasculature. According to other embodiments of the present invention, the implantable, multi-parameter sensor may be positioned in the peritoneal or may be positioned subcutaneously.

At step 62, a variety of parameters may be monitored in connection with myocardial infarction and angina using the implantable, multi-parameter sensor. According to embodiments of the present invention, lactate levels, blood oxygen saturation, base deficit and pH, for example, may be monitored in connection with myocardial infarction and angina. Also, these parameters may be continuously monitored. For example, potassium deficit has been linked with increased incidence of stroke in elderly individuals and an increase in atrial fibrillation after cardiac surgery.

At step 64, a risk may be assessed or a therapy administered for myocardial ischemia. Ischemic myocardium releases lactate in a quantitative relation to the extent of ischemia. At least one animal study has shown that 5-, 15- and 45 minute ischemic events result in 2.80, 9.27 and 6.11 mM blood lactate concentrations, respectively. Thus, the transition from myocardial ischemia to myocardial infarction and angina may be inferred from the shape of a blood lactate concentration curve with respect to time. Then, a state of myocardial infarction may be assessed and appropriate medication administered.

Figure 6:
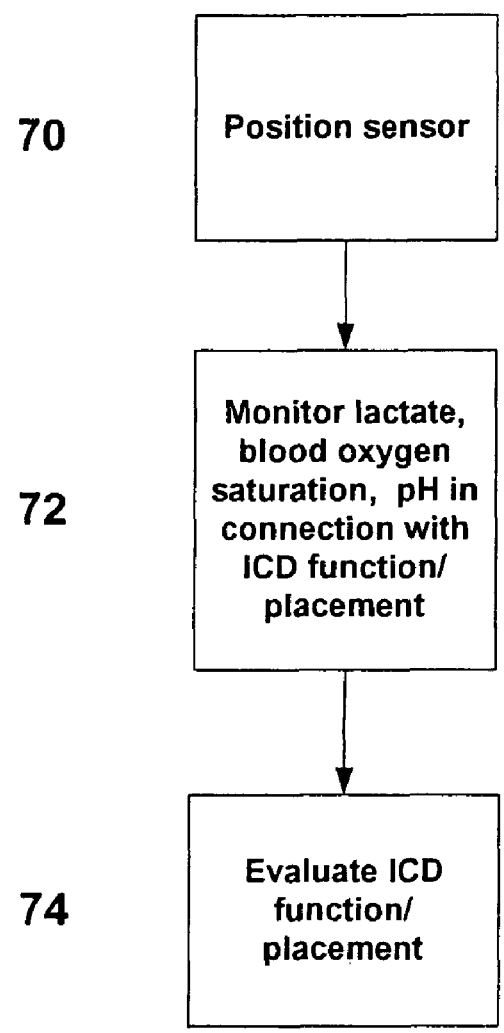
FIG. 6 shows another method for using an implantable, multi-parameter sensor according to an embodiment of the present invention.

A method for using an implantable, multi-parameter sensor in connection with the function and placement of an implantable cardiovascular defibrillator (ICD) according to an embodiment of the present invention is shown in FIG. 6. According to an embodiment of the present invention shown in FIG. 6, an implantable, multi-parameter sensor is positioned in a patient at step 70. The implantable, multi-parameter sensor may be inserted into the vasculature. According to other embodiments of the present invention, the implantable, multi-parameter sensor may be positioned in the peritoneal or may be positioned subcutaneously.

At step 72, a variety of parameters may be monitored in connection with the ICD using the implantable, multi-parameter sensor. According to embodiments of the present invention, lactate levels, blood oxygen saturation, base deficit and pH, for example, may be monitored in connection with the ICD in a patient. Also, these parameters may be continuously monitored.

At step 74, the function and placement of the ICD may be evaluated. For example, the trends in level and frequency of electrical shocks or pulses generated by the ICD relative to lactate levels, blood oxygen saturation, base deficit, blood pH or other parameters may be tracked and monitored. Depending on the efficacy of the ICD in connection with the levels of the monitored parameters, the functioning of the ICD may be adjusted to improve its effects. In addition, the appropriateness of the placement or positioning of the ICD may be evaluated. For example, the placement of the ICD may be adjusted if a medical professional determines that, given the frequency and levels of electrical shocks or pulses generated by the ICD relative to lactate levels, blood oxygen saturation, base deficit, blood pH or other parameters, a more advantageous position within the patient is desirable.

Figure 7:
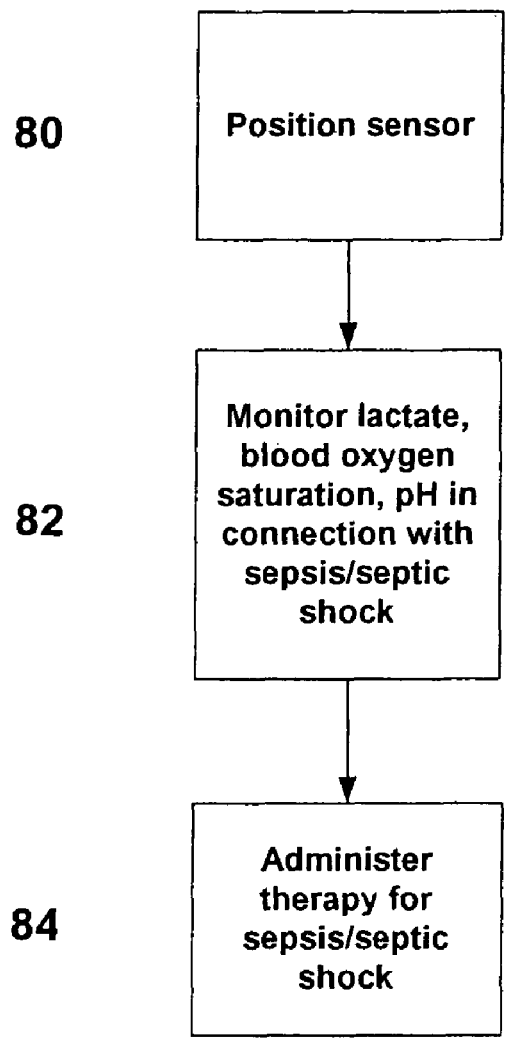
FIG. 7 shows another method for using an implantable, multi-parameter sensor according to an embodiment of the present invention.

A method for using an implantable, multi-parameter sensor in connection with sepsis or septic shock according to an embodiment of the present invention is shown in FIG. 7. Sepsis, defined by the presence of toxins from pathogenic organisms in the blood or tissue, often leads to global tissue hypoxia, multiple organ failure, such as sudden cardiovascular collapse, for example, and eventual death. Increased lactate concentrations and decreased mixed venous oxygen saturation are typical signs of early phases of septic shock. Lactate concentrations remain elevated throughout sepsis.

Sepsis is responsible for as many deaths as myocardial infarction. Severe sepsis and septic shock may be mitigated by using embodiments of the present invention. Severe sepsis and septic shock may be mitigated by continuously monitoring lactate levels in a patient. The concentration of lactate in the blood increases as a patient enters a septic phase. In addition, the concentration of blood potassium typically lowers as a patient enters a septic phase while central venous pressure drops. Also, according to some schools of thought, venous $O_2$ can rise as a patient becomes septic or is going through sepsis. Thus, embodiments of the present invention may be used to continuously monitor blood lactate, venous $O_2$, potassium and central venous pressure. According to embodiments of the present invention, sepsis and septic shock may be monitored using an implantable, multi-parameter sensor.

According to an embodiment of the present invention shown in FIG. 7, an implantable, multi-parameter sensor is positioned in a patient at step 80. The implantable, multi-parameter sensor may be inserted into the vasculature. According to other embodiments of the present invention, the implantable, multi-parameter sensor may be positioned in the peritoneal or may be positioned subcutaneously.

At step 82, a variety of parameters may be monitored in connection with sepsis or septic shock using the implantable, multi-parameter sensor. According to embodiments of the present invention, lactate levels, blood oxygen saturation, base deficit and pH, for example, may be monitored in connection with sepsis or septic shock in a patient. Also, these parameters may be continuously monitored.

At step 84, a risk may be assessed or a therapy administered for sepsis or septic shock. By continuously monitoring blood lactate, venous O2, potassium and central venous pressure, a physician or other medical attendant may administer to the patient responsive treatment based on the monitored parameters and prevent the patient from becoming septic.

Figure 8:
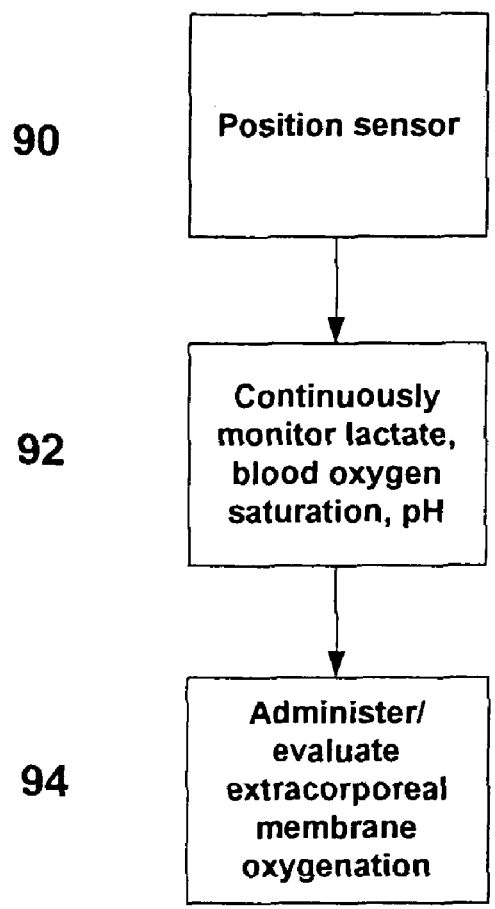
FIG. 8 shows another method for using an implantable, multi-parameter sensor according to an embodiment of the present invention.

A method for using an implantable, multi-parameter sensor in connection with ECMO according to an embodiment of the present invention is shown in FIG. 8. ECMO, a form of therapy supporting heart and lung functions in a patient when the patient's own heart and lung functions are inadequate, is typically administered from three to twenty-one days depending on the severity of the condition. Children typically require ECMO support from five to seven days. ECMO is typically performed on neonates but is also performed on adults. In ECMO, blood is drained from a patient through a catheter and is pumped through a membrane oxygenator serving as an artificial lung, adding oxygen into the blood and removing carbon dioxide from the blood. The blood then reenters the patient through a catheter placed in an artery. According to embodiments of the present invention, patient condition during ECMO therapy may be monitored using an implantable, multi-parameter sensor.

Also, hypoxia and hypertension are common not only in critically ill adults but also in sick neonates, particularly preterm infants receiving intensive care. Hyperlactataemia is associated with increased mortality in premature infants with respiratory distress syndrome (RDS) and respiratory failure patients receiving ECMO. Hyperlactataemia in neonates is defined as an arterial blood lactate concentration above 2.5 mM.

According to an embodiment of the present invention shown in FIG. 8, an implantable, multi-parameter sensor is positioned in a patient at step 90. The implantable, multi-parameter sensor may be inserted into the vasculature. According to other embodiments of the present invention, the implantable, multi-parameter sensor may be positioned in the peritoneal or may be positioned subcutaneously, or, for example, may be positioned in ventricular spaces, neurological spaces, such as the spine or brain, for example, intramuscular, myocardial, or pericardial spaces, and all vascular (venous and arterial) spaces. According to embodiments of the present invention, the implantable, multi-parameter sensor may also be position outside the body, for example, in an ECMO system.

At step 92, a variety of parameters may be monitored in connection with ECMO using the implantable, multi-parameter sensor. According to embodiments of the present invention, lactate levels, blood oxygen saturation, base deficit and pH, for example, may be monitored in connection with the administration of ECMO. Also, these parameters may be continuously monitored.

At step 94, a risk may be assessed or a therapy administered in connection with the administration of ECMO. By continuously monitoring blood lactate, blood oxygen saturation, base deficit, pH and other parameters, a physician or other medical attendant to may administer to the patient responsive treatment based on the monitored parameters and the effects of the ECMO.

Figure 9:
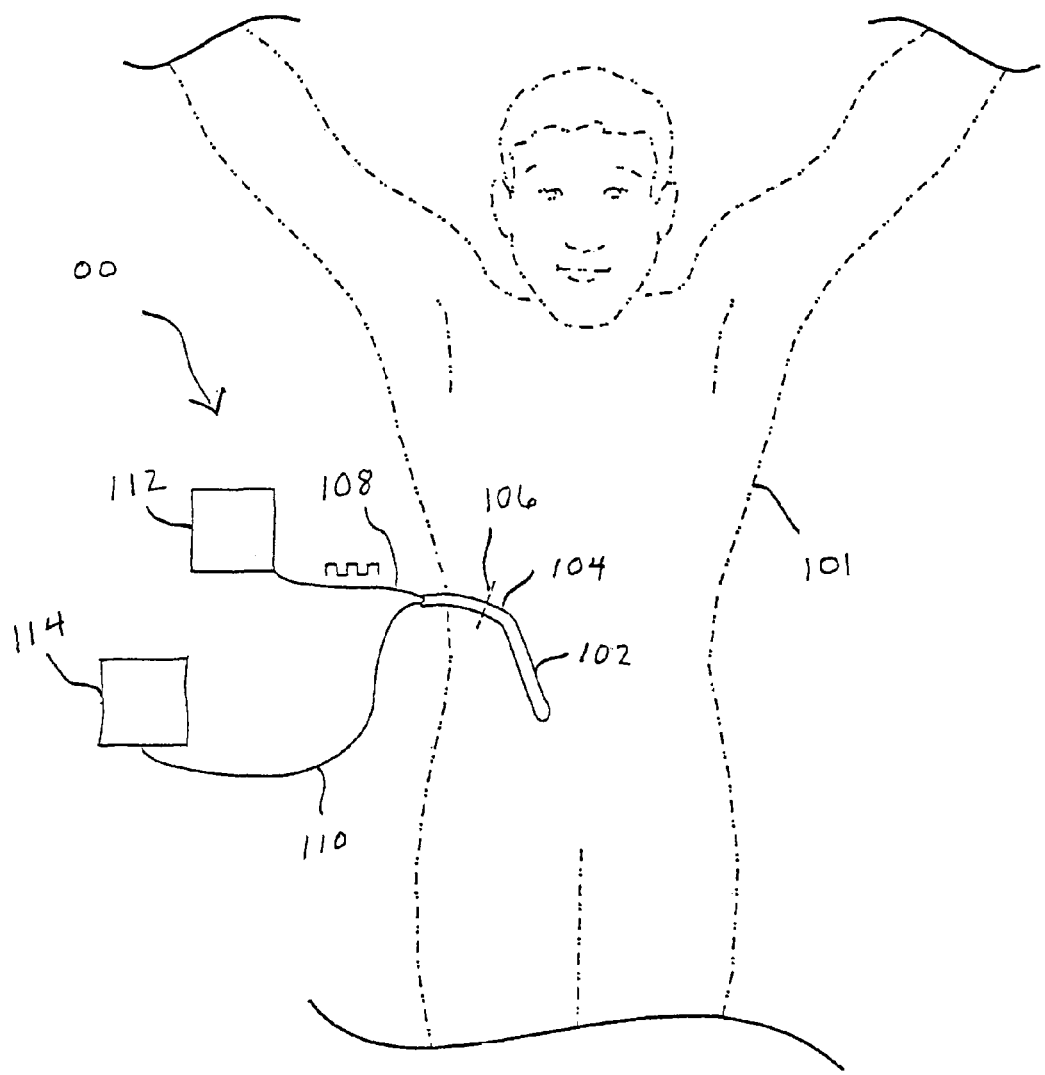
FIG. 9 shows a block diagram of an apparatus for sensing multiple parameters implanted in a patient according to an embodiment of the present invention.

A block diagram of a multi-parameter sensing system 100 with a multi-parameter sensor implanted in a patient may be seen in FIG. 9. In FIG. 9, an apparatus for sensing multiple parameters 102 is inserted into a patient 101. A catheter portion 104 of the apparatus for sensing multiple parameters 102 exits the patient 101 at an incision 106 and extends out of the patient 101. If the apparatus for sensing multiple parameters 102 shown in FIG. 9 is a daisy-chained apparatus, the information present on the interconnect 108 may be in digital form and may be connected directly to a computer 112 or other analytical device. The apparatus for sensing multiple parameters 102 in FIG. 9 may also include an infusion line 110 which may be connected to an infusant delivery system 114 or other delivery system.

Figure 10:
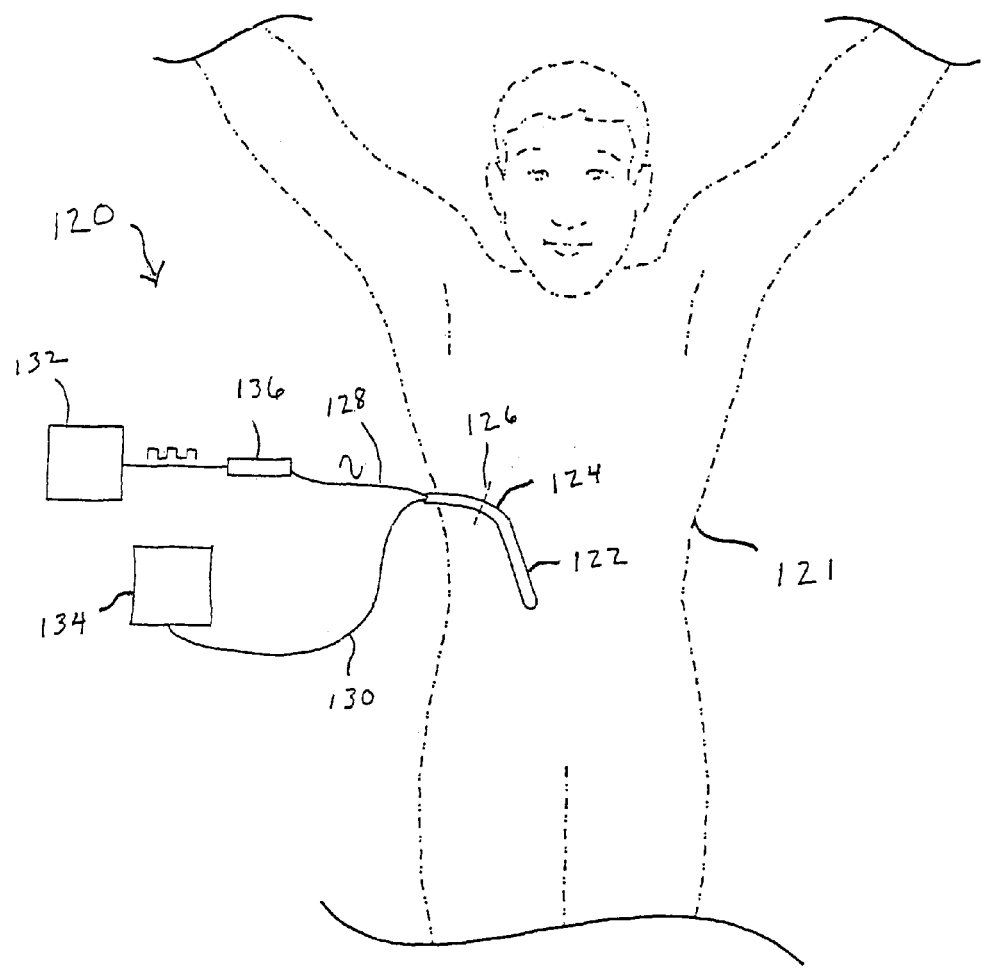
FIG. 10 shows a block diagram of another apparatus for sensing multiple parameters implanted in a patient according to an embodiment of the present invention.

A block diagram of a multi-parameter sensing system 120 according to another embodiment of present the present invention may be seen in FIG. 10. In FIG. 10, an apparatus for sensing multiple parameters 122 is implanted in a patient 121. A catheter portion 124 of the apparatus for sensing multiple parameters 122 exits the patient 121 at an incision 126 and extends out of the patient 121. In the embodiment of the invention shown in FIG. 10, if the apparatus for sensing multiple parameters 122 is a "wired" sensing apparatus, the information contained on the interconnect 128 may be in analog form. The interconnect 128, which may be a plurality of interconnects, may be connected to an analog-to-digital converter (A/D) 136. The information coming out of the A/D 136 is in digital form and may be connected to a computer 132 or other analytical device. According to another embodiment of the present invention, the information contained on the interconnect 128, being in analog form, may also be connected directly to an oscilloscope or other analytical device. The multi-parameter sensing system 120 may also include an infusion line 130 which may be connected to an infusant delivery system 134.

Figure 11:
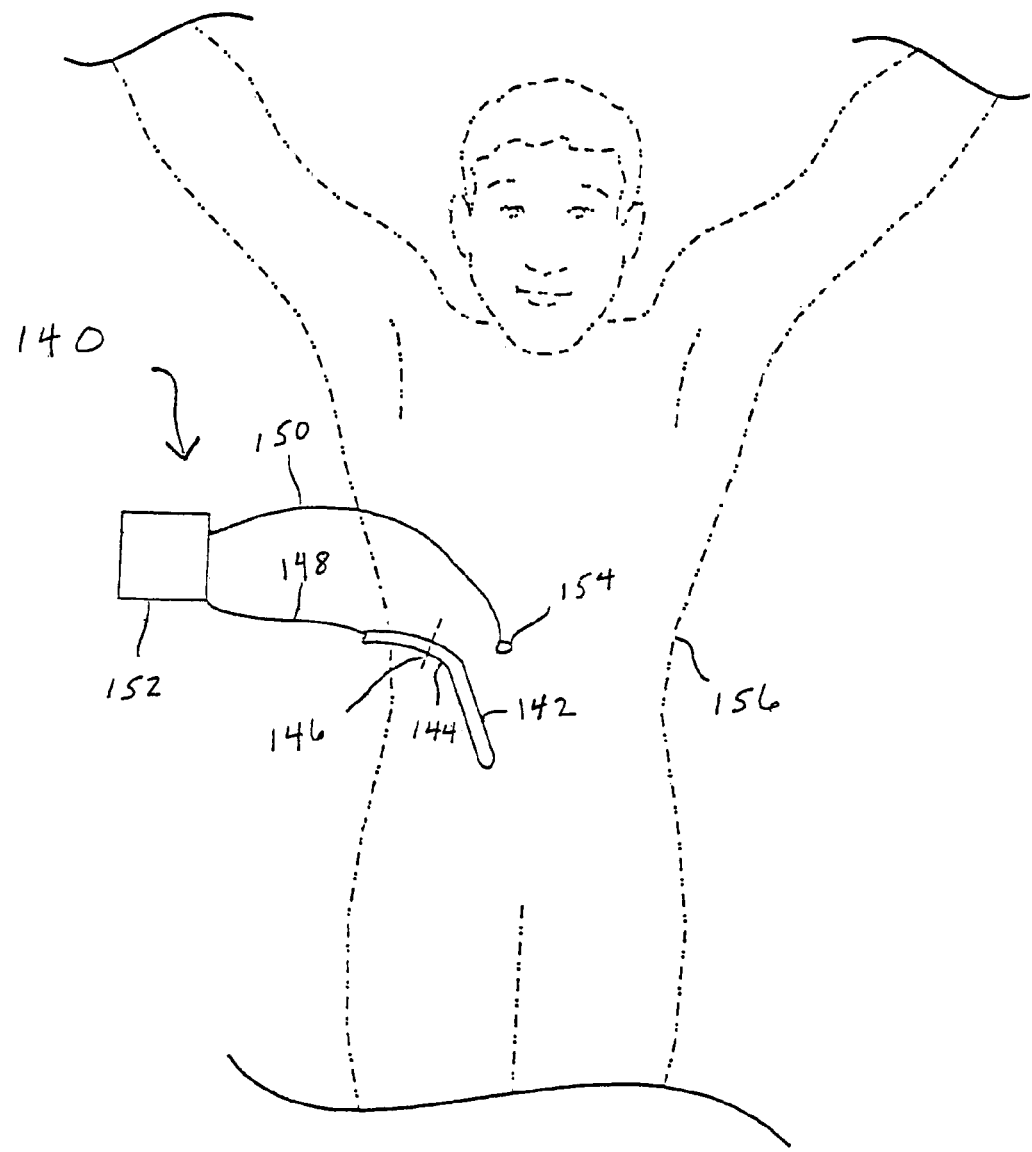
FIG. 11 shows a block diagram of another apparatus for sensing multiple parameters implanted in a patient according to an embodiment of the present invention.

A block diagram of a multi-parameter sensing system 140 according to another embodiment of present the present invention may be seen in FIG. 11. In FIG. 11, an apparatus for sensing multiple parameters 142 is implanted in a patient 156. A catheter portion 144 of the apparatus for sensing multiple parameters 142 exits the patient 156 at an incision 146 and extends out of the patient 156. In the embodiment of the invention shown in FIG. 11, one of the sensors in the apparatus for sensing multiple parameters 142 includes an internal electrode which cooperates with an external electrode 154. A first interconnect 148, which includes a signal from the internal electrode on one of the sensors in the apparatus for sensing multiple parameters 142, and a second interconnect 150 are connected to a computer or other controller/analyzer 152. The computer or other controller/analyzer 152 is able to sense a change of impedance between the internal electrode on one of the sensors in the apparatus for sensing multiple parameters 142 and the external electrode 154, corresponding to a change in the chemical, biological or physiological make-up of the area between the two electrodes, i.e., the patient.

For example, if a patient enters a state of edema, an increase in fluid in body tissue, the embodiment of the present invention shown in FIG. 11 could be used to detect the edema. An increase in fluid in body tissue may correspond to a change in the impedance of the body tissue, which would be sensed by the internal electrode and the external electrode 154. Edema is also associated with low sodium concentration or hyponatremia. Low sodium levels may cause body fluids to move into the higher osmolarity tissue, causing tissue to expand (edema). One clinical manifestation of this syndrome is increased brain pressure from cerebral edema.

Embodiments of the present invention may also be used to maintain proper insulin levels, especially in diabetics. For example, according to an embodiment of the present invention, blood glucose may be monitored and insulin levels adjusted accordingly to prevent a patient from becoming hypoglycemic or hyperinsulinemic. Along with glucose, $O_2$ and temperature measurements may be made to assist the medical professional in determining the most advantageous time and manner to adjust the patient's insulin to the proper levels.

Embodiments of the present invention allow medical professionals to use one sensing apparatus to measure multiple parameters. Thus, the medical and surgical risks involved by placing multiple devices or sensors on a patient to measure desired parameters are reduced.

Embodiments of the present invention may be used in vascular or non-vascular applications. For example, sensors according to embodiments of the present invention may be inserted into the vasculature. According to other embodiments of the present invention, sensors may be positioned in the peritoneal or may be positioned subcutaneously or, for example, may be positioned in ventricular spaces, neurological spaces, such as the spine or brain, for example, intramuscular, myocardial, or pericardial spaces, and all vascular (venous and arterial) spaces. According to embodiments of the present invention, the implantable, multi-parameter sensor may also be position outside the body, for example, in an ECMO system. Embodiments of the present invention may also be used for intracranial or defibrillation applications.

Embodiments of the present invention may also be used to classify the severity of a disease of a patient. For example, embodiments of the present invention may be useful in assisting physicians or other medical professionals in determining a patient's Simplified Acute Physiology Score (SAPS), Multiple Organ Disfunction Score (MODS) or other scoring index. In addition, embodiments of the present invention may be used in connection with grading systems such as the Acute Physiology and Chronic Health Evalutor (APACHE), for example.

Embodiments of the present invention may be used in a variety of environments. For example, embodiments of the present invention may be used in point-of-care testing or in a surgical, emergency, critical care or intensive care environment.

Embodiments of the present invention may also be used with other devices. For example, embodiments of the present invention may be used with heart pacemakers and defibrillators. In addition, embodiments of the present invention may be used in connection with internal or external pumps. For example, embodiments of the present invention may be used along with an implantable insulin pump.

While particular embodiments of the present invention have been shown and described, it will be obvious to those skilled in the art that the invention is not limited to the particular embodiments shown and described and that changes and modifications may be made without departing from the spirit and scope of the appended claims.

What is claimed is:

1. A method of sensing multiple parameters, the method comprising:

implanting an implantable sensor at a single site in a patient, the implantable sensor including a housing having an interior volume within which are disposed a plurality of implantable sensing elements, each implantable sensing element of the plurality of implantable sensing elements operable through electrical communication with an external controller via a respective interconnect of a plurality of interconnects, each respective interconnect of the plurality of interconnects independently connected to a respective implantable sensing element of the plurality of implantable sensing elements, each implantable sensing element of the plurality of implantable sensing elements located within the interior volume of the housing of the implantable sensor, each implantable sensing element of the plurality of implantable sensing elements for sensing within the interior volume of the housing of the implantable sensor at least one of a respective biological parameter, a respective physiological parameter, and a respective analyte; and reading an output from at least one implantable sensing element of the plurality of implantable sensing elements;

wherein a plurality of parameters are read from the implantable sensor at the single site;

wherein the output read from the at least one implantable sensing element of the plurality of implantable sensing elements is a quantifiable value; and wherein the plurality of interconnects are equal in number to the plurality of implantable sensing elements.

2. The method of claim 1, wherein at least one particular implantable sensing element of the plurality of implantable sensing elements is a biological parameter sensor.

3. The method of claim 1, wherein at least one particular implantable sensing element of the plurality of implantable sensing elements is a physiological parameter sensor.

4. The method of claim 1, wherein at least one particular implantable sensing element of the plurality of implantable sensing elements is an analyte sensor.

5. The method of claim 1, wherein reading an output from the at least one implantable sensing element of the plurality of implantable sensing elements comprises reading an output from an implantable sensing element of the plurality of implantable sensing elements that responds to lactate.

6. The method of claim 1, wherein reading an output from the at least one implantable sensing element of the plurality of implantable sensing elements comprises reading an output from an implantable sensing element of the plurality of implantable sensing elements that responds to blood oxygen saturation.

7. The method of claim 1, wherein reading an output from the at least one implantable sensing element of the plurality of implantable sensing elements comprises reading an output from an implantable sensing element of the plurality of implantable sensing elements that responds to blood pressure.

8. The method of claim 1, wherein reading an output from the at least one implantable sensing element of the plurality of implantable sensing elements comprises reading an output from an implantable sensing element of the plurality of implantable sensing elements that responds to glucose.

9. The method of claim 1, wherein reading an output from the at least one implantable sensing element of the plurality of implantable sensing elements comprises reading an output from an implantable sensing element of the plurality of implantable sensing elements that responds to temperature.

10. The method of claim 1, wherein reading an output from the at least one implantable sensing element of the plurality of implantable sensing elements comprises reading an output from an implantable sensing element of the plurality of implantable sensing elements that responds to potassium.

11. The method of claim 1, wherein reading an output from the at least one implantable sensing element of the plurality of implantable sensing elements comprises reading an output from at least one implantable sensing element of the plurality of implantable sensing elements that responds to pH.

12. The method of claim 1, further comprising administering therapy to the patient based on the output read from the at least one implantable sensing element of the plurality of implantable sensing elements.

13. The method of claim 12, wherein administering therapy comprises administering therapy for myocardial ischemia.

14. The method of claim 12, wherein administering therapy comprises administering therapy for myocardial infarction.

15. The method of claim 12, wherein administering therapy comprises administering therapy for angina.

16. The method of claim 12, wherein administering therapy comprises adjusting a function of an implantable cardiovascular defibrillator disposed within the patient.

17. The method of claim 12, wherein administering therapy comprises adjusting a placement of an implantable cardiovascular defibrillator disposed within the patient.

18. The method of claim 12, wherein administering therapy comprises administering therapy for sepsis.

19. The method of claim 12, wherein administering therapy comprises administering therapy for septic shock.

20. The method of claim 12, wherein administering therapy comprises administering therapy for a patient receiving extracorporeal membrane oxygenation.

21. The method of claim 12, wherein administering therapy comprises administering therapy for a patient undergoing cardiac bypass.

22. The method of claim 12, wherein administering therapy comprises administering therapy for a patient during dialysis.

23. The method of claim 1, further comprising classifying a severity of a condition of the patient based on the output read from the at least one implantable sensing element of the plurality of the implantable sensing elements.

24. The method of claim 1, wherein the patient is in a surgical environment.

25. The method of claim 1, wherein the patient is in an intensive care environment.

26. The method of claim 1, wherein each respective interconnect of the plurality of interconnects between each implantable sensing element of the plurality of implantable sensing elements and the external controller does not pass through any other implantable sensing element of the plurality of implantable sensing elements.

27. The method of claim 1,
wherein the external controller is external to the housing of the implantable sensor; and
wherein each respective interconnect of the plurality of interconnects between each implantable sensing element of the plurality of implantable sensing elements and the external controller is separate from all other interconnects for every other implantable sensing element of the plurality of implantable sensing elements on a corresponding communication path from each implantable sensing element of the plurality of implantable sensing elements to the external controller.

28. A method of claim 1, wherein each implantable sensing element of the plurality of implantable sensing elements is coupled by wire for electrical communication with the external controller.

29. The method of claim 1,
wherein each implantable sensing element of the plurality of implantable sensing elements of the comprises a respective power supply of a plurality of power supplies; and
wherein the respective power supply of each implantable sensing element of the plurality of implantable sensing elements is for powering the implantable sensing element.

30. The method of claim 1, the housing having an aperture for allowing each implantable sensing element of the plurality of implantable sensing elements to sense within the housing of the implantable sensor the at least one of a respective biological parameter, a respective physiological parameter, and a respective analyte.

31. The method of claim 30, the aperture for allowing fluid to pass into a volume inside the housing of the implantable sensor to allow each implantable sensing element of the plurality of implantable sensing elements to sense within the housing of the implantable sensor the at least one of a respective biological parameter, a respective physiological parameter, and a respective analyte.

32. The method of claim 1, wherein each implantable sensing element of the plurality of implantable sensing elements is disposed completely within the housing of the implantable sensor.

33. The method of claim 1, wherein each respective interconnect of the plurality of interconnects connects with the respective implantable sensing element inside the housing of the implantable sensor.

34. The method of claim 1, wherein the plurality of interconnects are equal in number to the plurality of implantable sensing elements in the interior volume of the housing of the implantable sensor.

35. The method of claim 1, wherein all of the implantable sensing elements are located in the interior volume of the housing.

36. The method of claim 1, wherein the exterior surface of the housing of the implantable sensor is free of the plurality of implantable sensing elements.

37. A method of evaluating a patient, the method comprising:
 implanting an implantable sensor in a patient, the implantable sensor including a housing having an interior volume within which are disposed a plurality of implantable sensing elements, each implantable sensing element of the plurality of implantable sensing elements operable through electrical communication with an external controller via a respective interconnect of a plurality of interconnects, each respective interconnect of the plurality of interconnects independently connected to a respective implantable sensing element of the plurality of implantable sensing elements, each implantable sensing element of the plurality of implantable sensing elements located within the interior volume of the housing of the implantable sensor, each implantable sensing element of the plurality of implantable sensing elements for sensing within the interior volume of the housing of the implantable sensor at least one of a respective biological parameter, a respective physiological parameter, and a respective analyte;
 reading an output from at least one implantable sensing element of the plurality of implantable sensing elements; and
 evaluating the patient based on the output read from the at least one implantable sensing element;
 wherein a plurality of parameters are read from the implantable sensor at a single site;
 wherein the output read from the at least one implantable sensing element of the plurality of implantable sensing elements is a quantifiable value; and
 wherein the plurality of interconnects are equal in number to the plurality of implantable sensing elements.

38. The method of claim 37, wherein evaluating the patient comprises evaluating the patient based on an output from a particular implantable sensing element of the plurality of implantable sensing elements that responds to lactate.

39. The method of claim 37, wherein evaluating the patient comprises evaluating the patient based on an output from a particular implantable sensing element of the plurality of implantable sensing elements that responds to blood oxygen saturation.

40. The method of claim 37, wherein evaluating the patient comprises evaluating the patient based on an output from a particular implantable sensing element of the plurality of implantable sensing elements that responds to blood pressure.

41. The method of claim 37, wherein evaluating the patient comprises evaluating the patient based on an output from a particular implantable sensing element of the plurality of implantable sensing elements that responds to glucose.

42. The method of claim 37, wherein evaluating the patient comprises evaluating the patient based on an output from a particular implantable sensing element of the plurality of implantable sensing elements that responds to temperature.

43. The method of claim 37, wherein evaluating the patient comprises evaluating the patient based on an output from a particular implantable sensing element of the plurality of implantable sensing elements that responds to potassium.

44. The method of claim 37, wherein evaluating the patient comprises evaluating the patient based on an output from a particular implantable sensing element of the plurality of implantable sensing elements that responds to pH.

45. The method of claim 37, wherein evaluating the patient comprises evaluating the patient for myocardial ischemia.

46. The method of claim 37, wherein evaluating the patient comprises evaluating the patient for myocardial infarction.

47. The method of claim 37, wherein evaluating the patient comprises evaluating the patient for angina.

48. The method of claim 37, wherein evaluating the patient comprises evaluating the patient having an implantable cardiovascular defibrillator.

49. The method of claim 37, wherein evaluating the patient comprises evaluating the patient for sepsis.

50. The method of claim 37, wherein evaluating the patient comprises evaluating the patient receiving extracorporeal membrane oxygenation.

51. The method of claim 37, wherein evaluating the patient comprises evaluating the patient while the patient is undergoing a cardiac bypass.

52. The method of claim 37, wherein evaluating the patient comprises evaluating the patient during dialysis.

53. The method of claim 37, wherein each respective interconnect of the plurality of interconnects between each implantable sensing element of the plurality of implantable sensing elements and the external controller does not pass through any other implantable sensing element of the plurality of implantable sensing elements.

54. The method of claim 37,
 wherein the external controller is external to the housing of the implantable sensor; and
 wherein each respective interconnect of the plurality of interconnects between each implantable sensing element of the plurality of implantable sensing elements and the external controller is separate from all other interconnects for every other implantable sensing element of the plurality of implantable sensing elements on a corresponding communication path from each the implantable sensing element of the plurality of implantable sensing elements to the external controller.

55. A method of claim 37, wherein each implantable sensing element of the plurality of implantable sensing elements is coupled by wire for electrical communication with the external controller.

56. The method of claim 37,
 wherein each implantable sensing element of the plurality of implantable sensing elements of the comprises a respective power supply of a plurality of power supplies; and
 wherein the respective power supply of each implantable sensing element of the plurality of implantable sensing elements is for powering the implantable sensing element.

57. A method of sensing multiple parameters, the method comprising:
 implanting an implantable sensor at a single site in a patient, the implantable sensor including a housing having an interior volume within which are disposed a plurality of implantable sensing elements, each implantable sensing element of the plurality of implantable sensing elements operable through electrical communication with an external controller via a respective one of a plurality of interconnects, each respective interconnect of the plurality of interconnects independently connected to a respective implantable sensing element of the plurality of implantable sensing elements, each of the implantable sensing element of the plurality of implantable sensing elements located within the interior volume of the housing of the implantable sensor, each implantable sensing element of the plurality of a parameter implantable sensing elements for sensing within the interior volume of the housing of the implantable sensor at least one of a respective biological parameter, a respective physiological parameter, and a respective analyte; and reading an output from at least one implantable sensing element of the plurality of implantable sensing elements;

wherein a plurality of parameters are read from the implantable sensor at the single site;

wherein the output read from the at least one implantable sensing element of the plurality of implantable sensing elements is a quantifiable value; and wherein the plurality of interconnects are equal in number to the plurality of implantable sensing elements.

58. The method of claim 57, wherein each implantable sensing element of the plurality of implantable sensing elements is operable through electrical communication with an external controller via a respective individual interconnect of a plurality of individual interconnects.

59. The method of claim 57, wherein each implantable sensing element of the plurality of implantable sensing elements allows for sensing at least one of a respective biological parameter, a respective physiological parameter, and a respective analyte.

60. A method of claim 57, wherein each implantable sensing element of the plurality of implantable sensing elements is electrically connected to an electrical conductor that extends out of the housing of the implantable sensor.

61. A method of claim 57, wherein each implantable sensing element of the plurality of implantable sensing elements is electrically connected to an electrical conductor that is electrically connectable to a remote device outside of the housing of the implantable sensor.

62. A method of claim 57, wherein each implantable sensing element of the plurality of implantable sensing elements is electrically connected to an electrical conductor that is electrically connectable to a controller.

63. The method of claim 57,
wherein each implantable sensing element of the plurality of implantable sensing elements of the comprises a respective power supply of a plurality of power supplies; and
wherein the respective power supply of each implantable sensing element of the plurality of implantable sensing elements is for powering the implantable sensing element.

64. A method of sensing multiple parameters, the method comprising:
implanting an implantable sensor at a single site in a patient, the implantable sensor including a housing having an interior volume within which are disposed a plurality of implantable sensing elements, each implantable sensing element of the plurality of implantable sensing elements operable through electrical communication with an external controller having a plurality of interconnects, each respective interconnect of the plurality of interconnects independently connected to a respective implantable sensing element of the plurality of implantable sensing elements, each implantable sensing element of the plurality of implantable sensing elements located within the interior volume of the housing of the implantable sensor, each implantable sensing element of the plurality of implantable sensing elements for sensing within the interior volume of the housing at least one of a respective biological parameter, a respective physiological parameter, and a respective analyte; and reading an output from at least one implantable sensing element of the plurality of implantable sensing elements;

wherein a plurality of parameters are read from the implantable sensor at the single site;

wherein the output read from said at least one implantable sensing element of the plurality of implantable sensing elements is a quantifiable value;

wherein the plurality of implantable sensing elements comprises at least one of a lactate sensing element for measuring a parameter for blood lactate level, a blood oxygen saturation sensing element for measuring a parameter for blood oxygen level, and a pH level sensing element for measuring a parameter for pH level; and wherein the plurality of interconnects are equal in number to the plurality of implantable sensing elements.

65. The method of claim 64, further comprising administering therapy for myocardial ischemia to the patient based on the output read from the at least one implantable sensing element.

66. The method of claim 64, further comprising administering therapy for myocardial infarction or angina to the patient based on the output read from the at least one implantable sensing element of the plurality of implantable sensing elements.

67. The method of claim 64, further comprising implanting an implantable cardiovascular defibrillator (ICD) into the patient and administering defibrillation on the patient based on the output read from the at least one implantable sensing element of the plurality of implantable sensing elements.

68. The method of claim 64, further comprising administering therapy for sepsis or septic shock to the patient based on the output read from the at least one implantable sensing element of the plurality of implantable sensing elements.

69. The method of claim 64, further comprising the step of administering therapy for extracorporeal membrane oxygenation (ECMO) to the patient based on the output read from the at least one implantable sensing element of the plurality of implantable sensing elements.

70. The method of claim 64,
wherein the external controller is external to the housing of the implantable sensor; and
wherein each respective interconnect of the plurality of interconnects between each implantable sensing element of the plurality of implantable sensing elements and the external controller is separate from all other interconnects of the plurality of individual interconnects on a corresponding communication path from each implantable sensing element of the plurality of implantable sensing elements to the external controller.

71. A method of claim 64, wherein each implantable sensing element of the plurality of implantable sensing elements is coupled by wire for electrical communication with the external controller.

* * * * *